United States Patent [19]

Green et al.

[11] Patent Number: 5,522,795
[45] Date of Patent: Jun. 4, 1996

[54] ENDOSCOPIC SWAB DEVICE

[75] Inventors: David T. Green, Westport; H. Jonathan Tovey, Milford; Ian M. Scott, Ridgefield; David A. Nicholas, Trumbull; Oleg Shikhman, Bridgeport, all of Conn.; William J. Francis, Quincy, Mass.

[73] Assignee: United States Surgical Corporation, Norwalk, Conn.

[21] Appl. No.: 7,941

[22] Filed: Jan. 25, 1993

[51] Int. Cl.⁶ ................................. A61B 10/00
[52] U.S. Cl. ................. 604/1; 128/759; 604/11
[58] Field of Search ................ 604/1–3, 11, 13, 604/15, 18, 256; 128/759

[56] References Cited

U.S. PATENT DOCUMENTS

| | | |
|---|---|---|
| 16,680 | 2/1857 | Russell . |
| 355,308 | 1/1887 | Foote . |
| 545,102 | 8/1895 | Sleem ........................... 604/15 |
| 682,090 | 9/1901 | Lee ............................... 604/13 |
| 685,088 | 10/1901 | Barlow . |
| 702,997 | 6/1902 | Pugh . |
| 1,131,349 | 3/1915 | Ellis . |
| 1,224,735 | 5/1917 | Gamache et al. . |
| 1,256,831 | 2/1918 | Rogers .......................... 604/1 |
| 1,523,943 | 1/1925 | Fowle . |
| 1,629,436 | 5/1927 | Capri . |
| 1,711,352 | 4/1929 | Jeffreys . |
| 1,858,694 | 5/1932 | Walsh . |
| 1,908,403 | 5/1933 | Budde ........................... 604/1 |
| 2,294,186 | 8/1942 | Kirschbaum ................... 604/1 |
| 3,896,552 | 7/1975 | Russell . |
| 4,023,559 | 5/1977 | Gaskell . |
| 4,136,680 | 1/1979 | Southwoeth . |
| 4,157,709 | 6/1979 | Schuster et al. . |
| 4,223,093 | 9/1980 | Newman et al. . |
| 4,234,673 | 11/1980 | Bucalo . |
| 4,283,809 | 8/1981 | Prost . |
| 4,457,313 | 7/1984 | Alter . |
| 4,586,604 | 5/1986 | Alter . |
| 4,653,510 | 3/1987 | Koll . |
| 4,813,432 | 3/1989 | Saint-Amand . |
| 4,877,036 | 10/1989 | Saint-Amand . |
| 4,877,037 | 10/1989 | Ko et al. . |
| 4,903,708 | 2/1990 | Saint-Amand . |
| 4,940,454 | 7/1990 | Siegausa . |
| 4,945,921 | 8/1990 | Okimoto . |
| 4,952,204 | 8/1990 | Koeteweg . |
| 5,031,635 | 7/1991 | Koll . |
| 5,074,840 | 12/1991 | Yoon ........................... 604/114 X |
| 5,080,659 | 1/1992 | Nakanishi . |
| 5,084,005 | 1/1992 | Kachigian . |
| 5,085,633 | 2/1992 | Hanifl et al. . |
| 5,125,897 | 6/1992 | Quinn et al. ................. 604/256 |
| 5,151,094 | 9/1992 | Hanifl . |
| 5,188,630 | 2/1993 | Christoudias . |
| 5,203,767 | 1/1993 | Cloyd ........................... 604/11 |
| 5,263,927 | 11/1993 | Shlain ........................... 604/13 |
| 5,295,952 | 3/1994 | Pietrafitta ...................... 604/15 |
| 5,308,316 | 5/1994 | Williams et al. . |

FOREIGN PATENT DOCUMENTS

1394925  5/1975  United Kingdom .

Primary Examiner—Mary Beth Jones
Assistant Examiner—Dennis Ruhl

[57] ABSTRACT

An endoscopic swab device comprising an elongated housing, a swab operatively associated with a distal end of the elongated housing and a connection member for connecting the swab relative to the housing and extending through the housing. A rotatable member is positioned on the housing to engage the connection member and further prevents separation of the swab from the housing. The tautness of the swab may be adjusted by rotating the rotatable member which positions the swab longitudinally relative to the elongated housing.

14 Claims, 7 Drawing Sheets

ENDOSCOPIC SWAB DEVICE

BACKGROUND OF THE INVENTION

1. Field of the Invention

The subject invention relates to surgical apparatus for performing endoscopic and laparoscopic surgical procedures, and more particularly, to surgical apparatus having a swab for abrasion or blunt dissection.

2. Description of the Related Art

In endoscopic and laparoscopic surgical procedures, a small incision or puncture is made in the patient's body to provide access for a trocar or cannula device. Once extended into the patient's body, the cannula allows insertion of various surgical instruments such as clip appliers, dissectors, scissors, forceps or graspers. It has thus become necessary for these instruments to have a configuration which can be inserted through the trocar housing and cannula.

One example of a swab is disclosed in U.S. Pat. No. 4,283,909 to Prost and is directed to a swab holding tool having a handle with tube mounted in a passageway thereof. The distal end of the tube includes a flared portion for holding a swab and indents for engaging a rod of the swab. Movement of the rod results in movement of the swab into and out of the tube. Another swab device for obtaining specimens is disclosed in U.S. Pat. No. 2,847,000 to Nieburgs. This device includes a tube having a plunger therein which is adapted for longitudinal and rotational movement. A swab is positioned at one end of the plunger, the overall length of which is greater than the length of the tube. Both of these references disclose devices for cleaning or sample collection.

An endoscopic swab device is disclosed in U.S. Pat. No. 5,074,840 to Yoon. This device discloses a packing device having a delivery tube and a rod attached to the proximal end of the gauze material. The rod deploys and manipulates the gauze material which absorbs liquid. Because of its flexibility this swab device is not well suited for abrading a sample.

It is desirable therefore, to provide an endoscopic swab device which can abrade or bluntly dissect a sample, such as tissue or an organ. It would also be desirable for the swab device to have an adjustable tautness. The device must also be adapted for insertion through a trocar and permit manipulation of the swab from an area remote to the area of operation, i.e., outside the body cavity. It would also be advantageous for the swab device to be simple and inexpensive to manufacture.

SUMMARY OF INVENTION

The subject invention provides a novel swab device for blunt dissection or abrading a sample during an endoscopic surgical procedure. The tautness of the swab in this device is adjustable. The device is also adapted and configured for unobstructed insertion through a trocar housing and cannula during endoscopic or laparoscopic procedures.

The endoscopic swab device in accordance with at least one embodiment of the present invention comprises an elongated housing having a connecting member extending therethrough. A swab is attached by sutures to the connecting member and extends from a distal end of the housing. A rotatable threaded member engages the threaded connecting member about the proximal end of the stem. Rotation of the rotatable member moves the swab longitudinally relative to the housing. The position of the swab relative to the housing affects the tautness of the swab and therefore its abrasiveness.

Further features of the swab device of the subject invention will become more readily apparent from the following detailed description of the invention.

BRIEF DESCRIPTION OF THE DRAWINGS

For a further understanding of the objects of the present invention, reference is made to the following detailed description of preferred embodiment which is to be taken in connection with the accompanying drawings, wherein.

DETAILED DESCRIPTION OF THE PREFERRED EMBODIMENTS

Laparoscopic procedures are by standard definition a subset of endoscopic procedures although these terms are often used interchangeably. Accordingly, the subject invention shall be discussed in terms of endoscopic procedures and apparatus. However, use herein of the terms such as "endoscopic", "endoscopically", and "endoscopic portion", among others, should not be construed to limit the present invention to an apparatus for use only in conjunction with an endoscopic tube. To the contrary, the subject invention may find use in any procedure in which access is limited to a small incision, including but not limited to laparoscopic procedures.

In the drawings and the description which follows, the term "proximal" will refer to the end of the apparatus which is closest to the operator while the term "distal" will refer to the end which is furthest from the operator.

Figure 1:
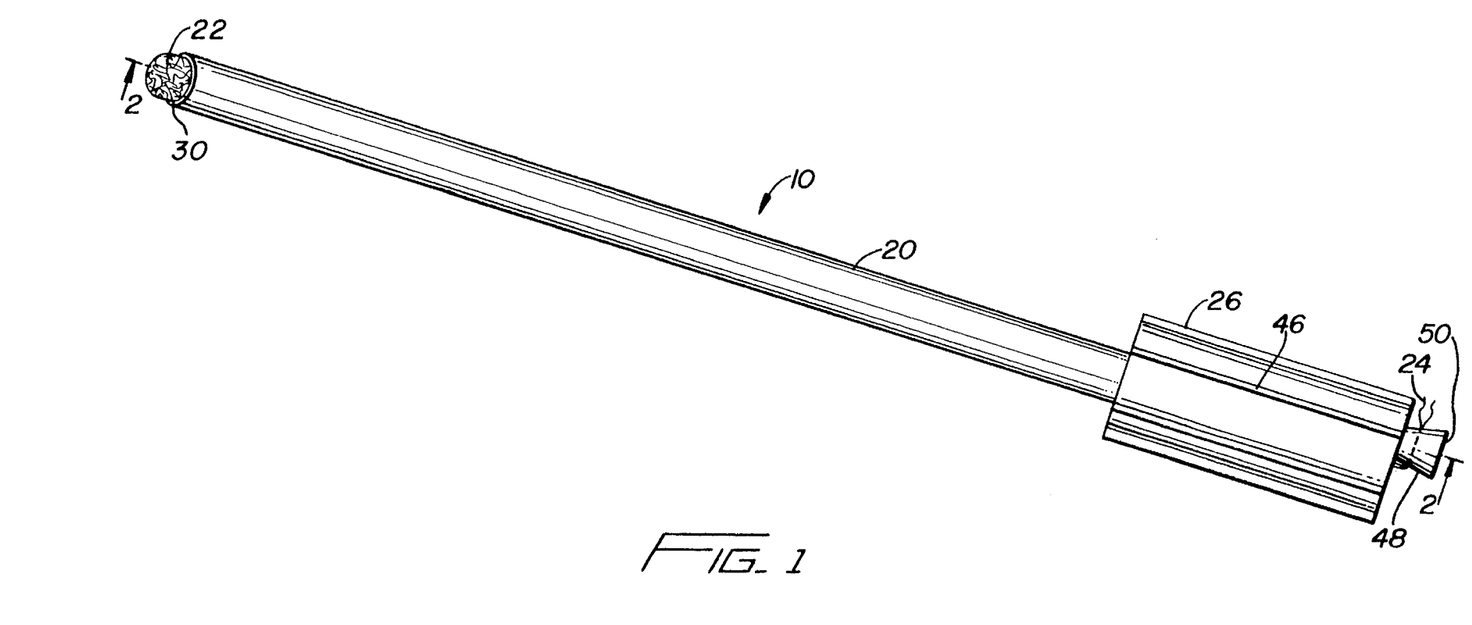
FIG. 1 is a perspective view of a device in accordance with the present invention.
Figure 2:
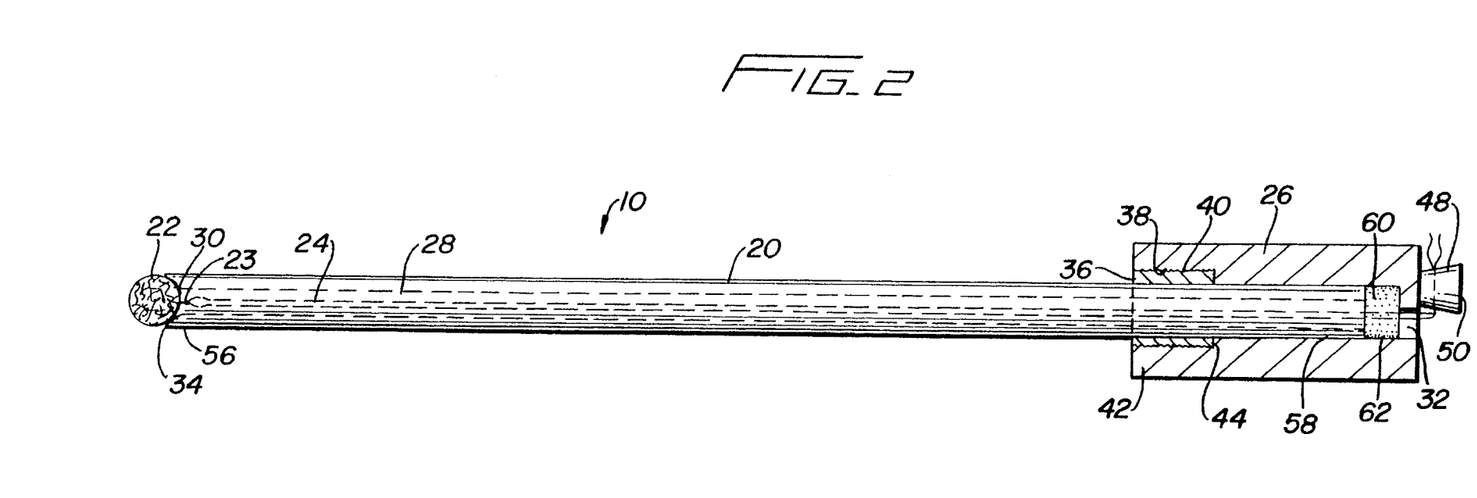
FIG. 2 is an elevational sectional view taken along the line 2—2 in FIG. 1.

Referring now in detail to the drawings in which like reference numerals identify similar or identical elements, a preferred embodiment of the swab device of the subject invention is illustrated in FIGS. 1 and 2, and is generally designated by reference numeral 10. Endoscopic swab device 10 comprises an elongated endoscopic portion 20, and a swab 22 which is attached to a suture 24. An end cap 26 retains the suture 24 and connects, or engages, the suture 24 and swab 22 with the endoscopic portion 20.

The endoscopic portion 20 which is in the form of an elongated tubular housing, stem or portion includes a passageway 28 extending therethrough from a distal end opening 30 to a proximal end opening 32 thereof. The distal opening 30 includes a countersunk hole 34 for receiving a portion of the swab 22 within the passageway 28 and thereby increasing the rigidity and stability of the swab 22 within the endoscopic portion 20 and avoiding possibility of fraying the suture. The hole 34 increases the stability and rigidity by allowing a portion of the swab 22 to rest in the hole 34. While in this embodiment the swab 22 is seated in a countersunk hole machined into the passageway, it would also be possible to provide a separate piece which could be fixedly attached in the passageway 28 near the distal end opening 30 and provide the same properties. Also, a deeper slot or hole 34 may be desired to resist sideway motion of the swab 22 during use. Sideway motion of the swab 22 could also be limited by adding glue to the hole 34 to limit lateral motion of the swab 22. The adjustability of swab tautness would be affected somewhat, however the swab 22 could still be pulled back into the distal opening 30 to affect tautness.

The proximal end opening 32 is adapted and configured to receive the suture 24 therethrough. Distal to the proximal opening 32 is an adapter 36 which is positioned around the endoscopic portion 20 and matingly engages the end cap 26. The adapter 36 includes a raised spiral portion 38 which matingly engages a spiral groove 40 formed in the inner surface of the end cap distal end 42. Rotation of the end cap 26 and the helical groove 40 along the spiral, raised portion 38 of the adapter 36 causes the suture 24 attached to the end cap 26 to move in a longitudinal direction. Thus, rotation of the end cap 26 results in tightening the suture 24 and positioning the swab 22 attached to the suture 24 within the endoscopic portion 20. The end cap 26 may be rotated along the adapter 36 until the cap 26 runs out of spiral, threaded, raised portion 38, thereby resulting in the end cap 26 being continuously rotated about the proximalmost raised portion 38 of the adapter 36 and also preventing inadvertent disengagement of the cap 26 from the endoscopic portion 20.

Figure 2A:
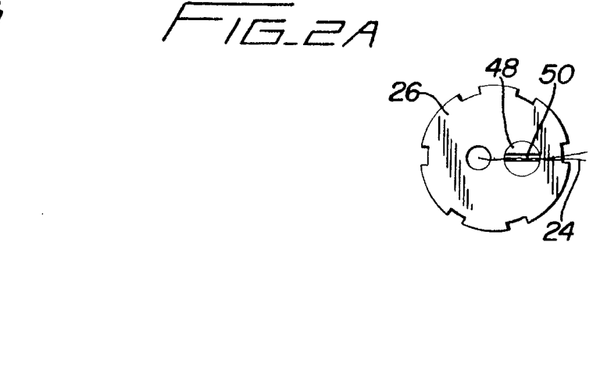
FIG. 2A is a front elevation view of the proximal end of the end cap of the device shown in FIG. 2.

As best seen in FIGS. 1 and 2A, the rotatable end cap includes a knurled surface 46 to enhance rotation of the cap 26 and, at its proximalmost end, a post 48 having a slit 50. The knurled surface 46 enables the user to better grip the end cap, and thereby enhance rotation of the end cap 26.

The swab 22 in this embodiment is a rosebud swab which is a spherical pre-tightened cotton gauze of simple, but denser than normal or twill, chevron weave. The swab 22 has a suture threaded therethrough, and is generally intended for abrading tissue during a surgical procedure. The suture or connection member 24 is attached to the swab 22 by inserting one end of the suture 24 through the swab 22. The suture is then tied into a knot 23 to prevent the swab 22 from traveling past the knot 23 in the suture 24. Other swabs, such as a Cherry Sponge or a "K" Dissector, could also be utilized for sample collection or for absorbing fluid during a surgical procedure.

In the embodiment shown in FIGS. 1 and 2, the suture 24 extends from the distal end 56 of the endoscopic portion 20, through the swab 22 and returns to the proximal end 58 of the endoscopic portion 20. As shown in the drawings the suture extends through the opening 32 in the endoscopic portion 20 and is wrapped around the post 48 and retained by a slit 50.

While in this embodiment the suture 24 acts as a connecting member, any type of string or elongated material could be used to connect and position the swab 22. Also, although the suture 24 in this embodiment is double stranded, it could also be, for example, single or triple stranded.

The swab device 10 also includes a foam seal 60 positioned in the proximal end 58 of the endoscopic portion 20 for preventing the escape of insufflation gas therethrough during endoscopic procedures. The suture 24 extends through a small opening 62 in the seal 60.

Figure 2B:
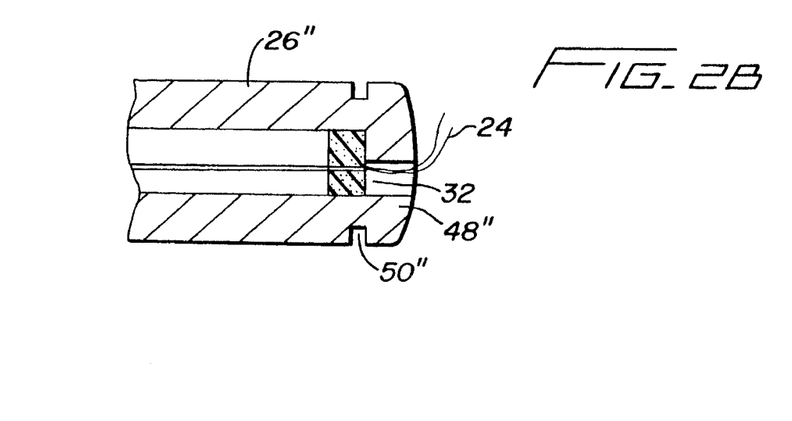
FIG. 2B is a cross-sectional view of the proximal end of an alternative end cap for the device shown in FIG. 2.

An alternative end cap 26''' is shown in FIG. 2B and includes a knob 48''' which is substantially the same diameter as the end cap 26''' with which it is integral. The suture 24 extends through an opening 32''' formed in the knob 48''' and is wrapped around circular slit 50''' to lock its position. A lateral slit is also included to for additional securement of the suture 24 to the end cap 26'''.

Figure 3:
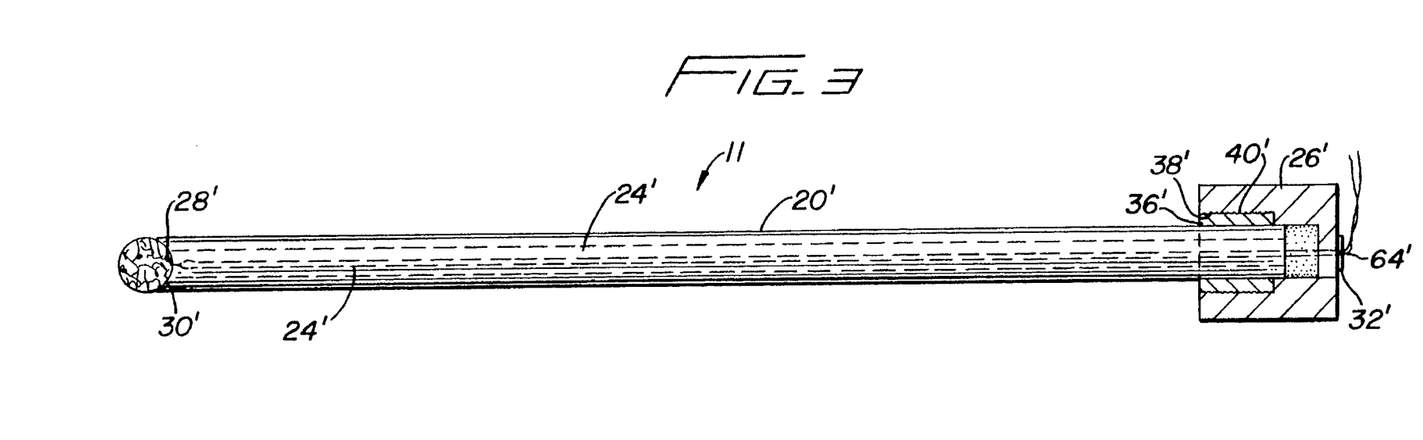
FIG. 3 is an elevational sectional view of an alternate apparatus in accordance with the present invention.

Referring to FIG. 3, another embodiment of the swab device 11 of the present invention is shown. In this embodiment the end cap 26' of swab device 11 includes an opening 32' which is only slightly larger in diameter than the diameter of the suture 24'. A suture anchor 64' is positioned adjacent the opening 32' to retain the suture 24' and prevent its disengagement from the end cap 26'. While this embodiment includes a suture anchor, it would also be possible to attach the suture to the end cap by an adhesive or a secure knot in the suture.

While each of the aforedescribed embodiments are intended to be 5 mm instruments, i.e. the outer diameter of the endoscope portion 20 would be approximately 5 mm, the device could also be used as a 10 mm instrument or in other diameters as well. It is contemplated that such a device could have an endoscopic portion with a swab spun around its distal end to form a tampon like member.

Figure 4:
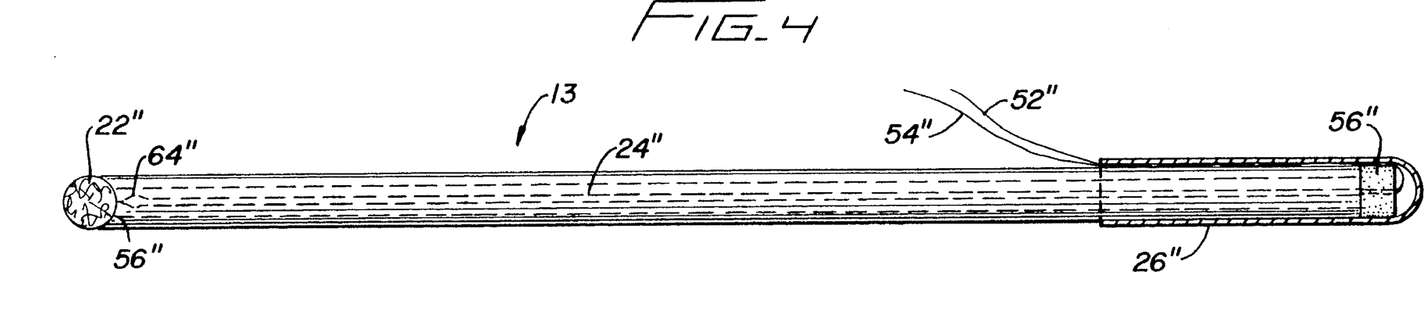
FIG. 4 is a side view of another alternate apparatus in accordance with the present invention.

In yet another embodiment, which is shown in FIG. 4, the swab device 13 includes an end cap 26" formed of flexible material and snugly fitting over the distal end 56" of endoscopic portion 20". The fit of the end cap 26" and endoscopic portion 20" is such that the suture 24" is retained by the cap 26" and cannot move relative to the endoscopic portion 20" without removing the end cap 26". In order to adjust the tautness of the swab 22", the end cap 26" is removed by pulling the cap 26" in the proximal direction. The suture 24" may then be pulled proximally to tighten it and increase the tautness of the swab 22", or released to loosen the suture 24" and reduce the tautness of the swab 22". The suture 24" is retained in its desired location by replacing the end cap 26" over the proximal end of the endoscopic portion 20" and over the suture 24" which has been positioned such that the swab 22" is of the desired tautness.

As shown in FIG. 4, an additional feature of this embodiment is the swab which is tubular in its original state, can be bent double, into a U-shape shown in the figure. A knot 64" keeps the swab in its U-shape and is formed in the suture 24" before its insertion into the endoscopic portion 20". Alternatively, the opposite sides of the U-shape may be sewn together, preferably with lock stitches. This horseshoe or U-shaped swab is commonly referred to as a Kittner Dissector.

In use, the swab device 10 is inserted into the body cavity through a cannula assembly of a trocar or directly through a small incision. While the use of the swab device 10 is described herein with respect to the first described embodiment, the other embodiments could also be used in the same manner. A laparoscopic camera will capture the entry and position of the apparatus in the body cavity, and this image will be reproduced on a monitor which the surgeon will be viewing. While following his or her movement on the monitor, the surgeon will be able to locate and position the swab device 10 at the body organ and tissue to be abraded. The surgeon then abrades the sample, or unwanted tissue, or other matter from the organ or tissue by brushing the swab against the object to be abraded. Depending on the desired swab tautness, which would relate to the fragility of organ and tissue to be abraded, the surgeon may rotate the end cap 26 to adjust the tautness of the swab 22. A sample or tissue which is sensitive or fragile would probably require a less taut swab than a sample or tissue which does not have those properties, or is difficult to remove. Once the desired swab tautness has been obtained, the suture 24 is wrapped around the post 48 and engaged in the slit 50 to prevent disengagement of the suture from the end cap 26.

In the event the surgeon would like to bluntly dissect the tissue or sample, the swab 22 abrades the desired sample and the surgeon then grasps the sample with another instrument such as an endoscopic grasper. The grasper with the sample can then be withdrawn through the trocar and transported to a laboratory for analysis.

The swab 22 and suture 40 are packaged in the endoscopic portion under normal tension, such that the swab has average tautness which may be adjusted in the above-identified manner. The swab device may be packaged as a single unit or in a multipack. Further, the swab device may be packaged as part of a kit for a cholecystectomy or other laparoscopic procedure.

Figure 5:
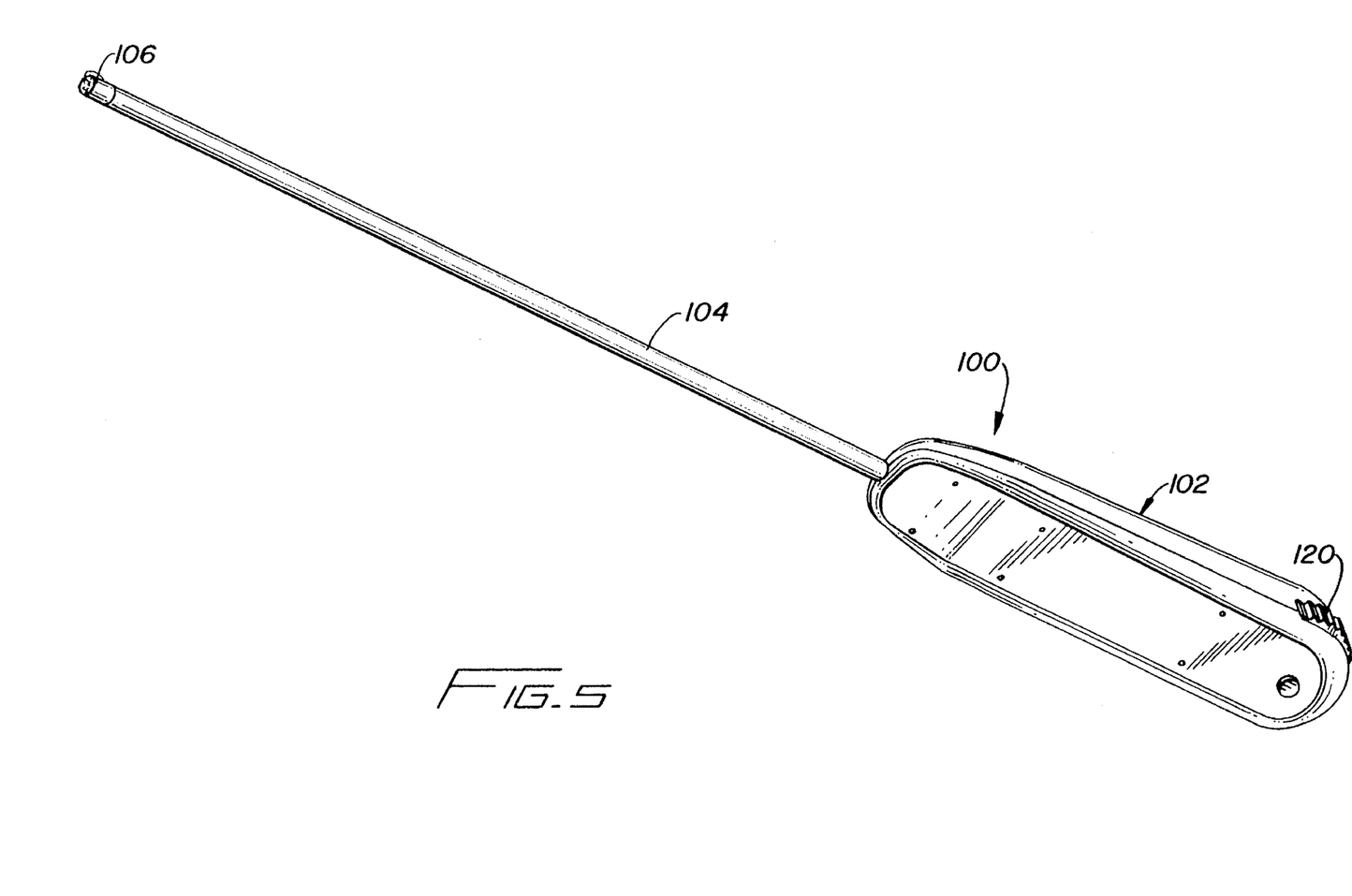
FIG. 5 is a perspective view of yet another alternate apparatus in accordance with the invention.
Figure 6:
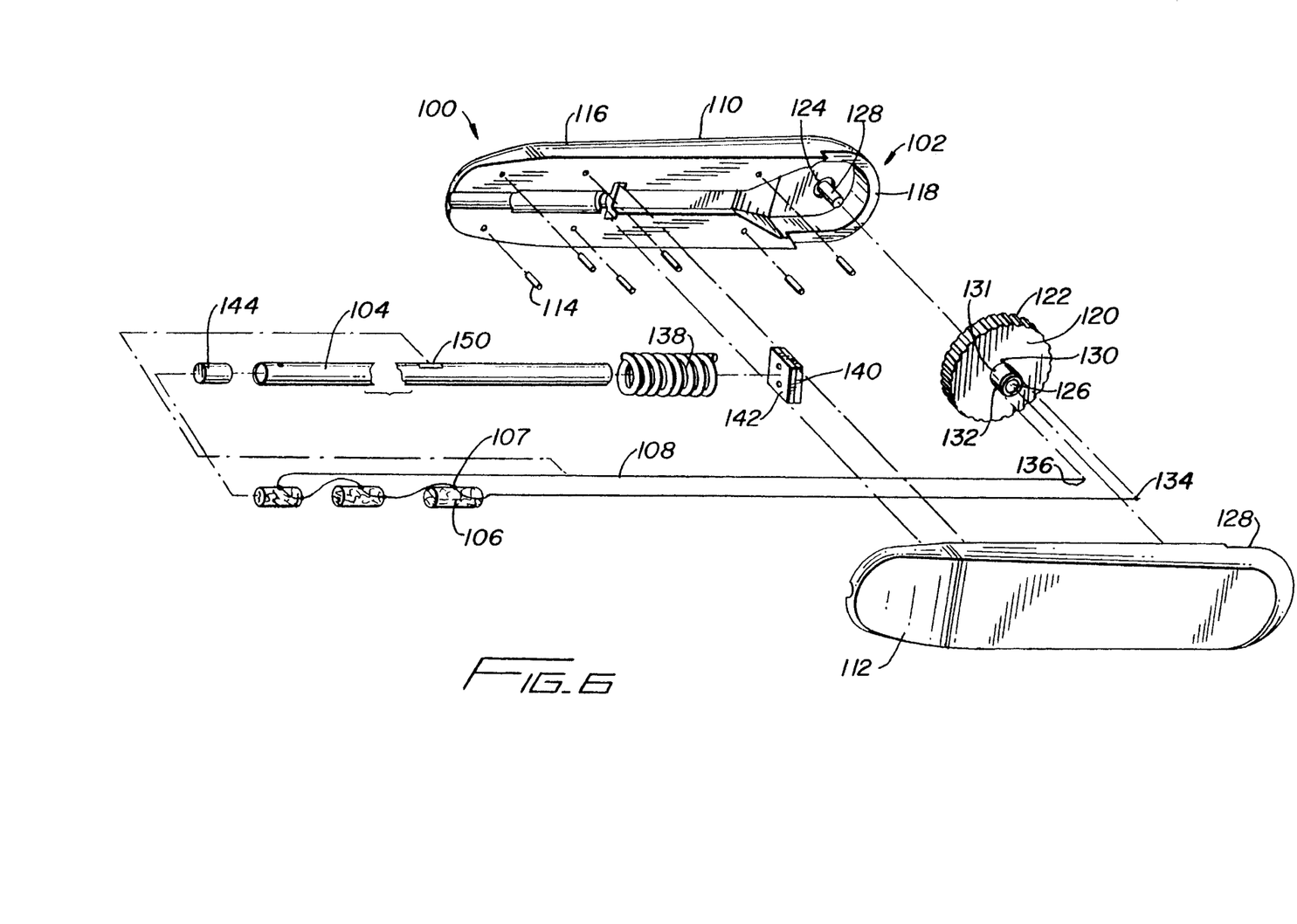
FIG. 6 is an exploded perspective view of the apparatus shown in FIG. 5.
Figure 7:
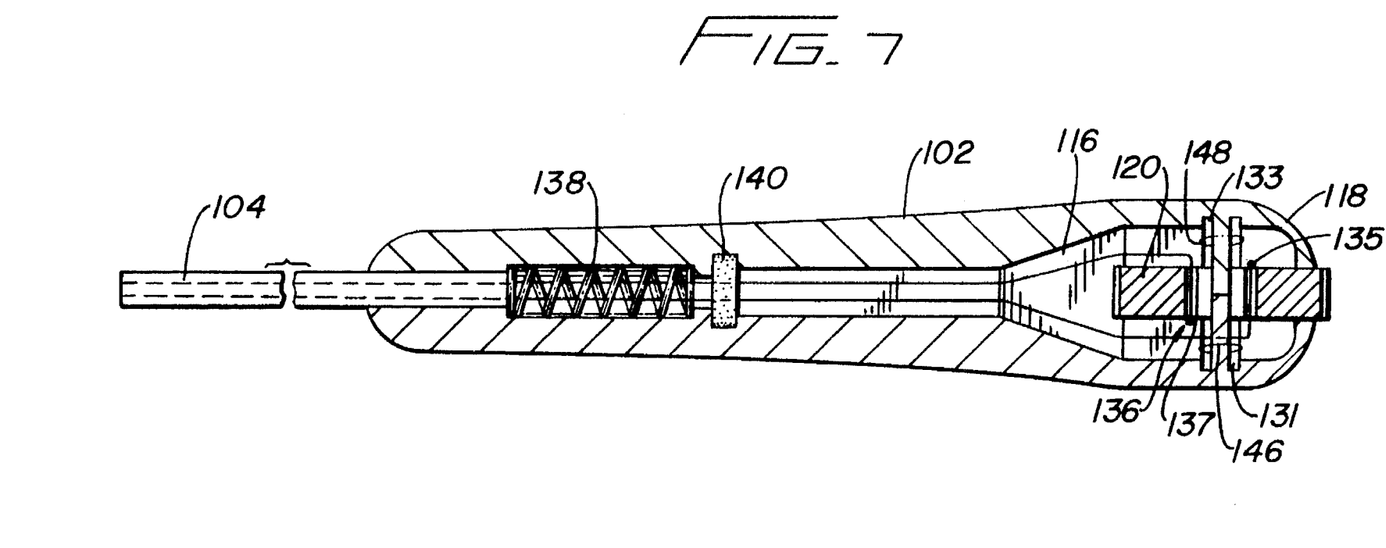
FIG. 7 is a side view of the handle of the apparatus shown in FIGS. 5 and 6.

Another embodiment of the swab device which is particularly adapted for supplying a plurality of swabs to the surgical site is shown in FIGS. 5 to 7. Referring particularly to FIGS. 5 and 6, the swab device 100 comprises a handle 102, an endoscopic elongated portion 104 and at least one swab 106 connected by a connecting member or suture 108 to the knob 120. The handle 102 is formed by a first housing 110 and a second housing 112. The housings 110 and 112 are positioned by pins 114 and their inner surfaces 116 are contoured and recessed so as to receive various components of the device as further explained below. The housings 110 and 112 are held together by an adhesive or may be welded or attached by screws.

The proximal end 118 of the handle 102 includes a knob 120 which adjusts and actuates the suture 108, and preferably includes a knurled surface 122 which enhances rotation by facilitating gripping. Extending from the inner surface 116 of the first housing 110 is a proximal end pin 124 which extends through and engages an opening 126 formed through the knob 120. The proximal ends 118 of handle housings 110 and 112 include radial cutouts 128 which are configured such that the knurled surface 122 of the knob 120 extends slightly beyond the proximalmost surface of the housings 110 and 112 to permit rotation of the knob 120 by the user. The knob 120 further includes a pair of oppositely positioned first and second openings 130 and 132 which receive a first end 134 and a second end 136, respectively, of the suture 108. A pair of radial flanges 131 extend from the knob 120 for positioning the knob 120 within the handle 102.

Figure 8:
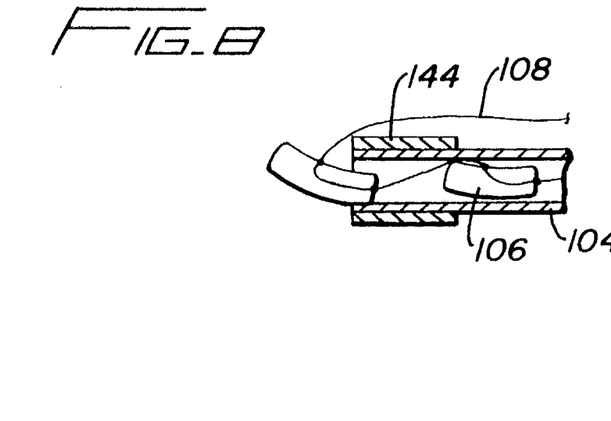
FIG. 8 is an exploded front view of the swab shown in Fig. 5.

The endoscopic or elongated portion 104 extends through and is retained within the handle 110. The endoscopic portion 104 further includes an opening 150 through which the suture 108 passes on its return to the handle 110. A spring 138, which in this embodiment is a compression coil spring, is positioned within the handle 110 and biases the suture 108 toward the distal end of the device 100 to keep the swab 106 and the suture 108 taut. A foam seal 140 is also positioned in the handle 110 to prevent the escape of insufflation gases. A pair of openings 142 are provided in the seal 140 to allow the suture 108 to pass through the seal 140. The distal end of the endoscopic portion 104 includes a seat 144 attached thereto. The seat 144 prevents the swabs 106 from fraying when they are bent (See FIG. 8) around the endoscopic portion 104.

In this device, the swab 106 is a Peanut swab which is a cotton gauze bag wrapped by a string. The connecting member or suture 108 is preferably attached through the proximal end of the proximalmost swab and out the middle of an upper portion 107 of that swab. That same suture 108 then is attached through the upper portion 107 of the next most distal swab and exits out the distalmost end of that swab. Alternatively the suture could pass through each swab in a straight line through its middle portion or through its top portion.

As stated earlier the suture 108 extends through the endoscopic portion 104, and begins and ends at first and second suture ends 134 and 136. As shown in FIG. 7, the first end 134 has a knot 135 formed therein which extends through the opening 130 and anchors that end of the suture in the knob 120 and further extends down the endoscopic portion 104. Extra suture 146 is wrapped around flange 131 and is supplied distally down the endoscopic portion 104 as the swabs are advanced distally. The second suture end 136 extends through opening 132 and terminates in a knot 137. A second flange 133 extends from the knob 120 and extra suture 148 (shown in phantom in FIG. 7) is wrapped around this flange when the knob 120 is rotated and extra suture 146 is unwrapped from flange 131.

In use, the swab device 100 is inserted into the body cavity through a cannula assembly of a trocar or directly through a small incision. A laparoscopic camera will capture the entry and position of the apparatus in the body cavity, and this image will be reproduced on a monitor which the surgeon will be viewing. While following his or her movement on the monitor, the surgeon will be able to locate and position the swab device 100 at the body organ and tissue to be dissected. The surgeon then rotates the knob 120 in a clockwise direction to advance the distal most swab 106 out of the endoscopic portion 104. The surgeon then bluntly dissects the tissue which is grasped by another instrument, such as a grasper, once that tissue has been dissected from its source. Once the swab 106 has been used, a clean swab can be advanced to the surgical site by further clockwise rotation of the knob. These steps can be repeated to advance additional clean swabs 106. This clockwise rotation will cause a portion of the extra suture 146 to unwrap from flange 131 and advance down the endoscopic portion, while a corresponding portion of suture 148 (shown in phantom in FIG. 7) will wrap around the opposite flange 133.

Also, this device could be used for abrasion. Once the abrasion or blunt dissection has been completed, or when all of the swabs 106 have been used, the distal most swab 106, as well as any other swabs, is retracted through the endoscopic portion 104 by rotating the knob 120 in a direction opposite to that used to advance the swabs distally.

Figure 9:
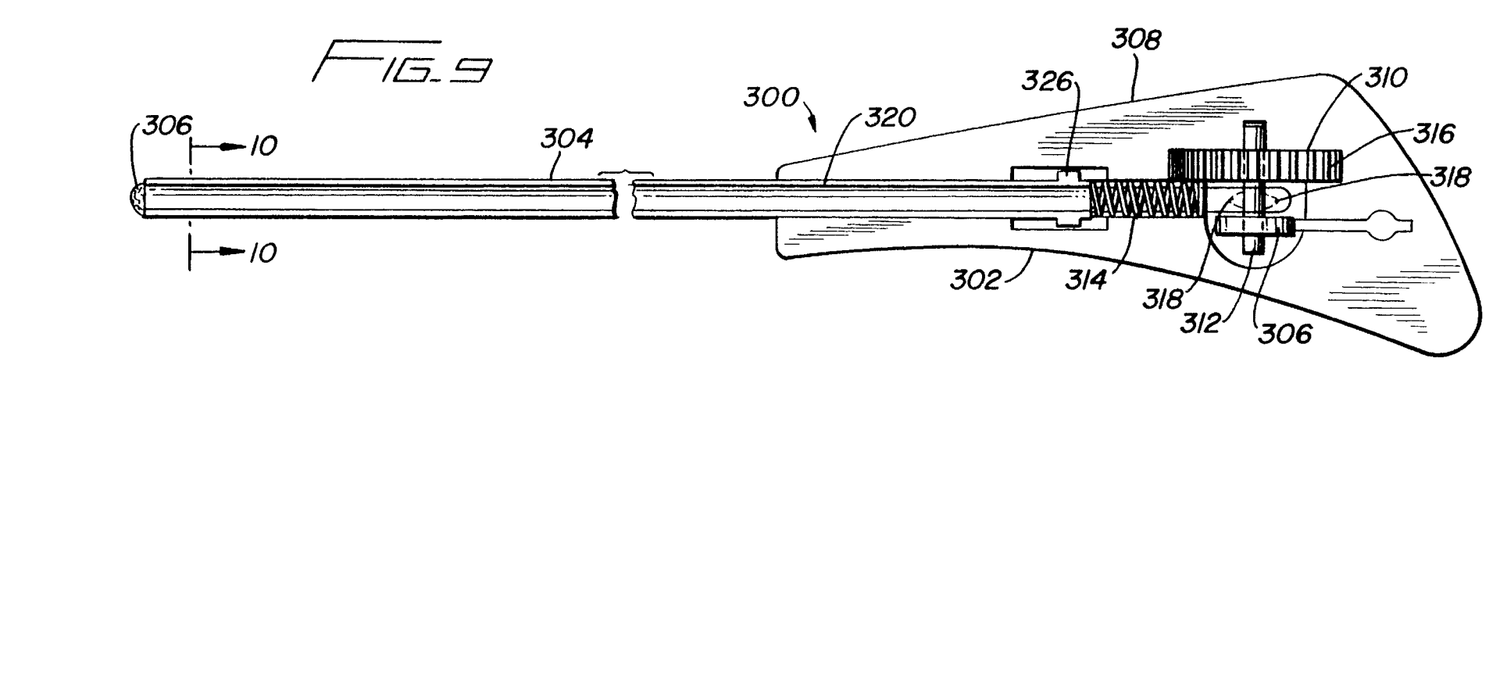
FIG. 9 is an elevational view of another alternative apparatus in accordance with the present invention.

Yet another embodiment of the invention is shown in FIG. 9 and is particularly directed to a swab device for supplying a continuous piece of gauze or swab to the surgical site for dissection, abrasion or absorption. The swab device 300 comprises a handle 302, an elongated endoscopic portion 304 and a swab or belt of gauze 306 engaged by the handle 302. The handle 302 includes a housing 308 which houses a rotating knob 310, an axle 312 and a compression spring 314. The knob 310 has a knurled surface 316 which enhances rotation by facilitating gripping. The axle 312 is attached to the knob 310 such that movement of the knob causes corresponding movement of the axle 312 and gauze 306. The axle 312 includes at least two gripping or engaging extensions 318 for engaging and rotating the gauze belt 306. The spring 314 biases the shaft 320 towards the distal end of the device to keep the gauze 306 taut. The handle knob 310 may also include a ratchet for limiting rotation of the knob 310 in only one direction.

Figure 10:
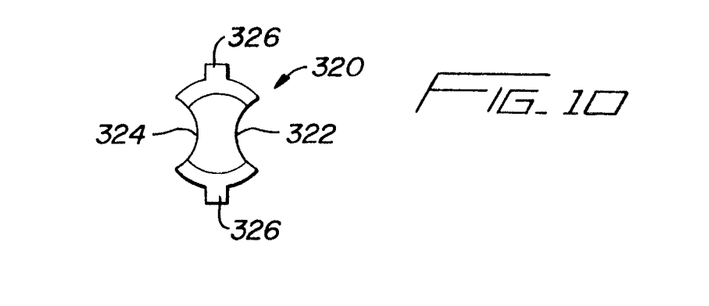
FIG. 10 is a cross-sectional view taken along the line 10—10 in FIG. 9.

The continuous belt of gauze extends from the handle 302 through the elongated portion 304 which includes a shaft 320 extending therethrough to guide the gauze 306 and prevent contamination of unused gauze 306. The shaft 320, best seen in FIG. 10, includes first and second cut out sections 322, 324, respectively, which each house opposite sections of the gauze 306 and prevent gauze contamination thereof. The shaft 320 is fitted into the handle 302 by flanges 326.

In use, the swab device 300 is inserted into the body as described with respect to the previous embodiment. Once the swab device 300 has been advanced to the surgical site and the distal gauze 328 extending from the elongated portion 304 has become saturated or used, clean, new gauze can be advanced to the surgical site by rotating the knob 310. This can be repeated as necessary.

It will be understood that the foregoing is illustrative of the principles of the invention and that various modifications can be made by those skilled in the art without departing from the scope and spirit of the present invention.

What is claimed is:

1. A swab device comprising:

an elongated housing;

a swab;

a connecting member configured and dimensioned to apply only a unidirectional longitudinal force to tension said swab, said connecting member being formed of flexible material and extending through said housing;

a retaining member retaining said connecting member and said swab relative to said housing wherein movement of said retaining member causes tensioning of said connecting member and said swab;

means for fixedly attaching a portion of said connecting member to said retaining member thereby preventing inadvertent detachment of said connecting member from said elongated housing; and a seal member positioned in said elongated housing; said seal member preventing escape of fluids therefrom.

2. A swab device as in claim 1 wherein said retaining member is positioned at a first end of said elongated housing which is opposite to a second end from which said swab extends.

3. A swab device as in claim 2 further comprising a seat in said second end of said elongated housing for stabilizing said swab relative to said elongated housing.

4. A swab device as in claim 1 wherein said connecting member is a suture.

5. A swab device as in claim 1 wherein said swab is composed of a material for abrading a tissue sample.

6. A swab device as in claim 1 wherein said rotatable member is attached to a proximal end of said elongated housing.

7. A swab device as in claim 1 wherein said swab is composed of a gauze material.

8. A swab device as in claim 1 wherein movement of said retaining member in a first direction retracts a portion of said swab into said elongated housing thereby increasing the tautness of said swab.

9. A swab device as in claim 1 wherein said retaining member is a rotating knob.

10. A swab device comprising:

a handle portion;

an elongated portion extending from said handle portion;

at least one swab, said at least one swab being attached to a suture material operatively associated with said handle portion and retaining said swab within a distal end of said elongated portion, said suture material extending through said elongated portion and being formed of flexible material configured and dimensioned to impart only a unidirectional force on said at least one swab in a single longitudinal direction to alter the tautness of said at least one swab;

a knob positioned in said handle portion and engaging said suture material for moving said at least one swab between a first position and a second position; and a seal member positioned in said handle portion, said seal member preventing escape of fluids therefrom.

11. A swab device as in claim 10 wherein said at least one swab is composed of a material for abrading a tissue sample.

12. A swab device as in claim 10 wherein said at least one swab is composed of a material configured and dimensioned for bluntly dissecting a tissue sample.

13. A swab device as in claim 11 wherein said swab has a curved configuration.

14. A swab device as in claim 12 wherein said swab has a U-shaped configuration which is formed by bending said swab about the distal end of said elongated portion.

* * * * *